Figure 1:
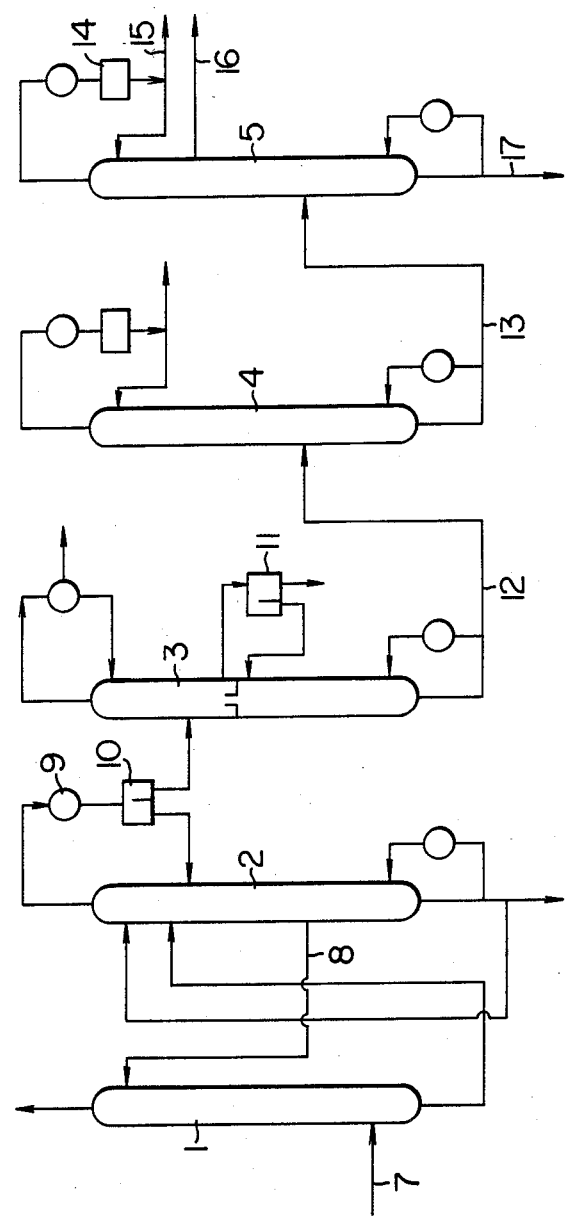

United States Patent [19]

Kawakami et al.

[11] Patent Number: 4,599,145

[45] Date of Patent: Jul. 8, 1986

[54] RECOVERY PROCESS FOR PRODUCING PURIFIED METHACRYLONITRILE

[75] Inventors: Kiyoshi Kawakami; Hiroyuki Ohashi; Tsutomu Katsumata, all of Yokohama, Japan

[73] Assignee: Asahi Kasei Kogyo Kabushiki Kaisha, Tokyo, Japan

[21] Appl. No.: 505,967

[22] Filed: Jun. 20, 1983

[30] Foreign Application Priority Data

Jun. 22, 1982 [JP] Japan .................. 57-107098

[51] Int. Cl.$^4$ .............................................. B01D 3/00
[52] U.S. Cl. ...................................... 203/71; 203/14; 203/61; 203/75; 203/DIG. 3; 203/DIG. 19; 203/99; 203/80; 203/78; 558/466
[58] Field of Search ................ 203/71, 14, 99, DIG. 3, 203/46, 75, 78, 80, 83, 85, 92, 95, 98, 57, 53, DIG. 19, 61, 73, 74, 76, 77, 79; 260/465.1, 465.3, 465.9

[56] References Cited

U.S. PATENT DOCUMENTS

| 3,196,085 | 7/1965 | Dippel .............................. 260/465.9 |
| 3,445,347 | 5/1969 | Borrel et al. .................. 203/DIG. 3 |
| 3,507,755 | 4/1970 | Bitners et al. .................... 260/465.9 |
| 3,862,890 | 1/1975 | Piesson et al. ......................... 203/71 |
| 3,936,360 | 2/1976 | Chih Wu ....................... 203/DIG. 3 |
| 4,166,008 | 8/1979 | Wu et al. ...................... 203/DIG. 3 |
| 4,269,667 | 5/1981 | Landis ............................... 260/465.9 |
| 4,294,665 | 10/1981 | Issei et al. ..................... 203/DIG. 3 |
| 4,377,444 | 3/1983 | Wu .................................. 260/465.9 |

FOREIGN PATENT DOCUMENTS

| 0527220 | 7/1956 | Canada ............................... 260/465.9 |
| 0000566 | 2/1979 | European Pat. Off. ......... 260/465.3 |
| 0012039 | 1/1980 | European Pat. Off. ......... 260/465.9 |
| 0053518 | 6/1982 | European Pat. Off. ......... 260/465.9 |

*Primary Examiner*—S. Leon Bashore
*Assistant Examiner*—V. Manoharan
*Attorney, Agent, or Firm*—Pennie & Edmonds

[57] ABSTRACT

Methacrylonitrile higher in purity than that obtained by the conventional process is efficiently produced by the present improved process for producing purified methacrylonitrile in which the reaction mixture formed by the ammoxidation of isobutylene or tert-butyl alcohol is distilled using water as solvent to obtain a crude methacrylonitrile solution which contains methacrylonitrile as major constituent, methacrolein, hydrogen cyanide, and isobutyronitrile, and the crude methacrylonitrile solution is then purified in a product column, wherein the improvement comprises first removing isobutyronitrile from said crude solution, then feeding the remaining solution to the product column, withdrawing from the top a vapor containing methacrolein, condensing the vapor, returning a greater part of the condensate to the product column while removing the remainder from the distillation system, and withdrawing purified methacrylonitrile from the middle or lower section, preferably from a point lower than the feeding stage.

9 Claims, 2 Drawing Figures

RECOVERY PROCESS FOR PRODUCING PURIFIED METHACRYLONITRILE

This invention relates to a process for the production of methacrylonitrile and, more particularly, to a process for producing methacrylonitrile by the ammoxidation of isobutylene or tert-butyl alcohol.

It is known that methacrylonitrile is formed by the gas phase catalytic reaction of isobutylene or the like with ammonia and oxygen. The reaction product contains by-products such as methacrolein, hydrogen cyanide, and isobutyronitrile in addition to methacrylonitrile. The by-products, methacrolein and hydrogen cyanide, combine to form methacrolein cyanohydrin, a labile, high-boiling condensation product (boiling at 95° C./13 mmHg). Accordingly, when it is attempted to purify the reaction mixture by distillation, methacrolein cyanohydrin is formed in the isolation step of methacrylonitrile. In the subsequent distillation step, the cyanohydrin is decomposed again into methacrolein and hydrogen cyanide which contaminate the distillate, thus decreasing the purity of methacrylonitrile. For this reason, it has heretofore been difficult to obtain a high-purity product.

The purification of methacrylonitrile has heretofore been carried out according to the conventional process for producing acrylonitrile. An example of the conventional process is as shown in FIG. 1. The ammoxidation products absorbed in absorption water, comprising methacryonitrile as the major constituent, are subjected together with solvent water to extractive distillation in a recovery column 2. The overhead vapor is condensed in a condenser 9 and the condensate is sent to a decanter 10, where the oil layer is separated. This layer is a liquid comprising, in addition to methacrylonitrile, impurities such as methacrolein, hydrogen cyanide, isobutyronitrile and the like and is saturated with water. The oil layer is then sent to a de-hydrogen cyanide-dehydration column 3 and a low-boiling fraction-separating column 4, in which low-boiling components such as water, hydrogen cyanide, methacrolein and the like are separated therefrom to obtain crude methacrylonitrile containing a decreased amount of low-boiling fraction. This crude methacylonitrile is sent to a product column 5, where the low-boiling fraction contained in a slight amount and the high-boiling fraction are removed through lines 15 and 17, respectively, while the product methacrylonitrile is obtained through line 16. However, methacrolein and hydrogen cyanide partially form methacrolein cyanohydrin which cannot be completely removed in the de-hydrogen cyanide-dehydration column and the low-boiling fraction-separating column. A part of the cyanohydrin is incorporated into the fed to the product column, where it is decomposed again into methacrolein and hydrogen cyanide which contaminate the product and deteriorate the purity thereof. As compared with the acrolein formed in the production of acrylonitrile, the reason why the methacrolein formed as by-product in the production of methacrylonitrile specifically becomes a problem is that methacrolein is formed as by-product in larger amounts than acrolein. Moreover, owing to its lower susceptibility to hydration or polymerization, it remains in the reaction system in a higher concentration without disappearing.

In order to solve the above problem, several proposals have hitherto been made. For instance, British Pat. No. 1,350,486 discloses a proposal for the removal of hydrogen cyanide and a carbonyl compound as a side stream from an intermediate stage of the recovery column in order not to bring methacrolein cyanohydrin to the subsequent distillation step. However, in order to remove exhaustively the low-boiling hydrogen cyanide as a side stream from the recovery column, there are needed a large steam consumption and installation of a distillation column of large diameter which requires an increased investment. Moreover, if it is intended to utilize the hydrogen cyanide in said side stream, it is needed to increase the number of plates of a stripping pot or to increase further the steam consumption.

For the purpose of protecting the product methacrylonitrile from contamination with methacrolein and hydrogen cyanide formed by the decomposition of cyanohydrin, proposals have been made for the stabilization of cyanohydrin by the use of stabilizers such as oxalic acid (Japanese Patent Publication No. 10,112/64), sulfamic acid or ammonium hydrogensulfate (Japanese Patent Publication No. 28,316/64), sulfamic acids or aromatic sulfonic acids. This method is effective when the cyanohydrin content is low, but when the content is large, the cyanohydrin is accumulated particularly when continuous distillation is effected, and consequently, the content becomes large and the effect of the method on increasing the product purity is low.

Japanese Patent Publication No. 18,126/68 discloses a modified process in which in the first step cyanohydrin is decomposed in the presence of a chemical and the resulting acroleins and hydrogen cyanide are removed by distillation and in the second step a chemical is added to stabilize the residual cyanohydrin, which is then removed by distillation. Such a procedure is effective in the batch distillation before the cyanohydrin has been concentrated. However, in the continuous distillation or in the case of considerable accumulation of cyanohydrin in batch distillation, it becomes necessary to add an increased amount of a known inorganic or organic acid which offers problems regarding the material constructing the equipment and the disposal of the acid. The research of the present inventors has revealed that such a process is not economically favorable, because in order to achieve a desirable result in continuous distillation it is necessary to withdraw a large amount of liquid from the enriching section so as to keep the cyanohydrin concentration from increasing.

As described above, there is no report on the commercially established process for producing high-purity methacrylonitrile from crude methacrylonitrile containing methacrolein and hydrogen cyanide. The present inventors have carried out extensive research with special attention to the above problems. This invention has been achieved based on the discovery that the presence of by-product isobutyronitrile accelerates the decomposition of methacrolein cyanohydrin, as a result of extensive research.

According to this invention, there is provided an improved process for producing purified methacrylonitrile in which the ammoxidation products of isobutylene or tert-butyl alcohol are distilled using water as a solvent to obtain a crude methacrylonitrile solution containing methacrylonitrile as the major constituent, methacrolein, hydrogen cyanide, and isobutyronitrile, and the crude methacrylonitrile solution is then purified in a product column, wherein the improvement comprises first removing isobutyronitrile from said crude methacrylonitrile solution, feeding the remaining solution to the product column, withdrawing from the top a vapor containing methacrolein, condensing the vapor, returning the condensate to the product column except for a minor portion which is removed from the distillation system, and withdrawing purified methacrylonitrile from the middle or lower section of the product column.

The invention is described below in detail with respect to the accompanying drawings. In the drawings, FIG. 1 is a flow sheet illustrating a conventional process for the production of methacrylonitrile and FIG. 2 is a flow sheet illustrating an example of the embodiment of this invention.

Figure 2:
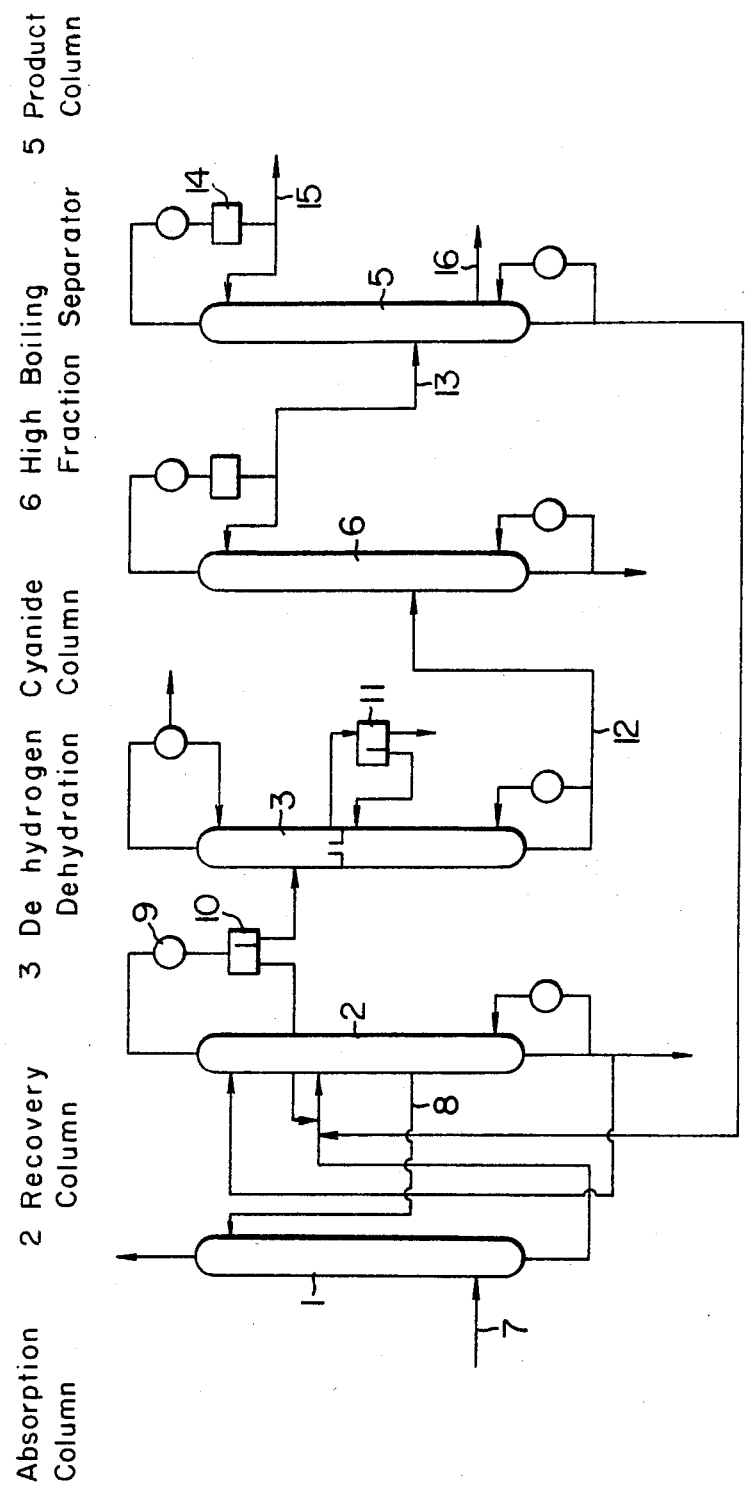

In FIGS. 1 and 2, 1 is an absorption column, 2 a recovery column, 3 a de-hydrogen cyanide-dehydration column, 4 a low-boiling fraction-separating column, 5 a product column, 6 a high-boiling fraction-separating column, 7 a gaseous reaction mixture line, 8 a lower section line of the recovery column, 9 a condenser, 10 and 11 decanters, 12 a bottom line of the dehydration column, 13 a feed line of the product column, 14 a decanter, 15 an overhead line of the product column, 16 a product methacrylonitrile-withdrawing line, and 17 a lower section line of the product column.

The decomposition of methacrolein cyanohydrin is markedly accelerated in the presence of isobutyronitrile, as shown later in Example 3. In the conventional process, since the by-product isobutyronitrile is not removed, it remains in the ammoxidation reaction mixture in a concentration of about 2,000 ppm and is sent to the product column, where it accumulates at the bottom during distillation and accelerates the decomposition of methacrolein cyanohydrin. To the contrary, in the process of this invention, since a crude methacrylonitrile solution substantially free of isobutyronitrile is fed to the product column, the methacrolein cyanohydrin, if formed in a minute amount, is hardly decomposed during distillation and the contamination of product methacrylonitrile with methacrolein and hydrogen cyanide is markedly reduced.

In an embodiment of this invention as shown in FIG. 2, a high-boiling fraction-separating column 6 is provided before the product column 5, where the product methacrylonitrile is separated by distillation. The recovered solution from the recovery column 2 is sent to the de-hydrogen cyanide-dehydration column 3 where most of the hydrogen cyanide and water are removed, the remainder being sent to the high-boiling fraction-separating column 6. This column 6 is operated under such predetermined conditions that the number of plates and the reflux ratio are set to meet the requirements for the separation of isobutyronitrile (boiling at 103.5° C.) from methacrylonitrile. Isobutyronitrile is substantially removed by withdrawing from the bottom methacrylonitrile containing, beside isobutyronitrile, high-boiling fraction such as methacrolein cyanoydrin, acids and polymerization inhibitor. Crude methacrylonitrile is obtained as overhead vapor and is sent to the product column 5 where the low-boiling fraction is removed through an overhead line 15 and the product methacrylonitrile is withdrawn as a gas-phase stream through the withdrawing line 16 located at the lower section of the column.

In the present process, the removal of isobutyronitrile can be performed not only in the high-boiling fraction-separating column, as in the above example, but also in other steps prior to the product column under properly selected conditions. For instance, isobutyronitrile can be substantially removed by operating the recovery column 2 under such conditions that isobutyronitrile can accumulate in the bottom, withdrawing the isobutyronitrile-concentrated solution from the lower section line 8 of recovery column for use as the absorption water in the absorption column 1, and stripping the isobutyronitrile into the off-gas line. In manufacturing acrylonitrile, no detectable amount of by-product isobutyronitrile is formed, whereas in the production of methacrylonitrile, isobutyronitrile exists generally in a concentration of several thousands ppm in the recovered solution from the recovery column. In the present process, the concentration of isobutyronitrile in the feed stream to the product column should be preferably 200 ppm by weight or less, more preferably 100 ppm by weight or less, and most preferably 50 ppm by weight or less. Such a low isobutyronitrile content of the feed makes it possible to reduce the contaminant methacrolein content in the product methacrylonitrile to 100 ppm by weight or less, preferably 50 ppm by weight or less, as determined in terms of total aldehyde content. The purity of product methacrylonitrile varies depending upon the methacrolein and hydrogen cyanide content in the feed to the product column and the distillation conditions.

The formation of methacrolein cyanohydrin takes place markedly in the condensate of the vapor generated by distilling off methacrolein in which condensate methacrolein is enriched. This condensate generally contains water dissolved therein, and is separated into an oil layer and an aqueous layer. The formation of cyanohydrin is accelerated particularly in the aqueous layer, and is accelerated also in the oil layer with an increase in water content. Accordingly, the formation can be suppressed by decreasing the water content in said condensate. The formation is also suppressed by controlling the pH of the condensate. By maintaining the pH of the condensate within the range of from 1.0 to 4.5, preferably from 1.5 to 4.0, it is possible to suppress efficiently the formation of cyanohydrin and, hence, to improve the quality of product methacrylonitrile. The suppression of cyanohydrin formation becomes more effective when the pH is regulated and, at the same time, the water content is previously reduced, whereby the water content in the condensate is made below saturation, that is, the condensate is allowed to contain water in such an amount that the condensate does not separate into an oil layer and an aqueous layer.

An embodiment of the present invention is shown in FIG. 2. In this example of the process, the water content of the crude methacrylonitrile is kept at 0.2% by weight or less in the feed line 13 to the product column by properly controlling the degree of dehydration in the de-hydrogen cyanide-dehydration column 3, thereby keeping the condensate of the vapor distilled out of the top of product column 5 from separating into an oil layer and an aqueous layer in the decanter 14. Moreover, an organic acid is added to the decanter 14 to adjust the pH to 1.0–4.5 in order to suppress the formation of cyanohydrin. Under the above operation conditions, the formation of cyanohydrin at the top of product column is very slight. Moreover, the high-boiling fraction such as cyanohydrin and isobutyronitrile which accelerates the decomposition of cyanohydrin is largely removed in the preceding high-boiling fraction-separating column. Therefore, the formation as well as decomposition of cyanohydrin hardly takes place in the product column, resulting in an improvement in product quality.

In the present process, among organic acids suitable for use in adjusting the pH, acetic acid and propionic acid are preferred in view of the ease of handling and the cost. It is convenient to add the acid for pH adjustment to the decanter 14, though it may be added to the top of the column where methacrolein is separated by distillation. The pH measurement is performed in the oil layer in case the condensate separates into an oil layer and an aqueous layer. When the layer separation does not occur, the measurement is performed, of course, in the homogeneous phase.

EXAMPLE 1

Ammoxidation products of isobutylene or tert-butyl alcohol were distilled using water as a solvent. Methacrylonitrile, methacrolein, hydrogen cyanide, cyanohydrin, and isobutyronitrile were recovered as distillate. An organic layer was separated from the distillate in a decanter. The organic layer was fed at a rate of 560 ml/hr to a middle stage of a de-hydrogen cyanide column of 25 mm in internal diameter and 400 mm in height at atmospheric pressure. The low-boiling fraction such as hydrogen cyanide was removed as overhead stream. The bottom stream was separated in a decanter into an aqueous layer and an organic layer, and the latter was fed to the upper stage of a dehydration column of 25 mm in internal diameter and 350 mm in height. The overhead stream was returned to the still of the de-hydrogen cyanide column. The bottom stream from the dehydration column was crude methacrylonitrile having its water content reduced to 0.075% by weight. The temperature conditions of both columns were as follows: in the de-hydrogen cyanide column, 30°–31° C. at the top and 75°–77° C. at the bottom; in the dehydration column, 70°–73° C. at the top and 88°–92° C. at the bottom. The crude methacrylonitrile was fed at a rate of 110 ml/hr to a high-boiling fraction-separating column of 32 mm in internal diameter and 55 in number of plates, at a pressure of 400 mmHg, the feeding point being located at a height of one-third of the column. From the bottom, methacrylonitrile containing high-boiling fractions such as methacrolein cyanohydrin, isobutyronitrile, acetic acid, and a polymerization inhibitor was withdrawn at a rate of 2–7 ml/hr. The bottom temperature of the high-boiling fraction-separating column was 87°–89° C. and the overhead gas temperature was 71°–73° C. The overhead distillate was fed at a rate of 100 ml/hr to a middle stage of a product column of 32 mm in internal diameter and 70 in number of plates at a pressure of 575 mmHg. Low-boiling fractions such as methacrylonitrile and the like were removed as overhead distillate and the product methacrylinitrile was withdrawn from the lower section as a gas phase stream. In the product column, the bottom temperature was 83°–86° C. and the temperature of overhead gas stream was 69°–72° C. The compositions of the feed to the high-boiling fraction-separating column and the side gas stream of the product column were as shown in Table 1.

TABLE 1

| | Feed to high-boiling fraction separating column (crude methacrylonitrile ppm (wt.) | Side gas stream from product column (product methacrylonitrile) ppm (wt.) |
|---|---|---|
| Methacrolein | 20,700 | 43 |

TABLE 1-continued

| | Feed to high-boiling fraction separating column (crude methacrylonitrile ppm (wt.) | Side gas stream from product column (product methacrylonitrile) ppm (wt.) |
|---|---|---|
| Acrylonitrile | 7,600 | 21 |
| Acetonitrile | 830 | Trace |
| Hydrogen cyanide | 0 | 27 |
| Cyanohydrin | 9,800 | 0 |
| Propionitrile | 47 | 35 |
| Isobutyronitrile | 1,650 | Trace |
| Water | 750 | 90 |

COMPARATIVE EXAMPLE 1

In the same manner as in Example 1, crude methacrylonitrile having a reduced hydrogen cyanide and water content was obtained as the bottom stream from the dehydration column. The crude material was fed at a rate of 130 ml/hr to the 45th plate of a low-boiling fraction-separating column of 70 in number of plates and 32 mm in internal diameter at a pressure of 300 mmHg, to remove low-boiling fractions such as methacrolein and acrylonitrile. The bottom temperature was 66°–68° C. and the temperature of overhead gas stream was 48°–52° C. The bottom stream was fed at a rate of 150 ml/hr to the 30th plate of a product column of 55 in number of plates and 32 mm in internal diameter at a pressure of 350 mmHg. High-boiling fractions such as isobutyronitrile, methacrolein, cyanohydrin, and polymerization inhibitor were removed as bottom stream at a rate of 14 ml/hr, while the product methacrylonitrile was withdrawn as a liquid side stream from the 50th plate at a rate of 134 ml/hr. Temperature conditions: the bottom temperature 76°–78° C.; the overhead gas temperature, 57°–59° C.; the liquid side stream temperature, 61°–62° C. The impurities content of the product methacrylonitrile and that of the intermediate stage products were as shown in Table 2.

TABLE 2

| | | | Unit: ppm (wt.) |
|---|---|---|---|
| | Feed to low-boiling fraction-separating column (crude methacrylonitrile) | Liquid side Bottom stream from a low-boiling-fraction-separating column | stream from product column (product methacrylonitrile) |
| Methacrolein | 14,900 | ≈0 | 2,360 |
| Acrylonitrile | 7,990 | 140 | 45 |
| Hydrogen cyanide | ≈0 | ≈0 | 1,150 |
| Cyanohydrin | 17,900 | 6,580 | 420 |
| Isobutyronitrile | 1,540 | 1,340 | 10 |
| Water | 700 | 150 | 60 |

EXAMPLE 2

A liquid material containing methacrylonitrile as the major constituent, methacrolein, isobutyronitrile, and hydrogen cyanide and saturated with water was fed to a de-hydrogen cyanide-dehydration column, as in Example 1, whereby the hydrogen cyanide and water were removed and crude methacrylonitrile was obtained. The crude material was fed to a high-boiling fraction-separating column to remove high-boiling fractions including isobutyronitrile and then fed to a product column. The product methacrylonitrile was obtained as a gas-phase stream from a lower section of the column.

When the isobutyronitrile content in the feed to the product column was varied, there were found significant differences in methacrolein content and hydrogen cyanide content in the product. Further, the effect of pH was examined by adding acetic acid to the condensate of overhead gas stream from the product column. The results obtained were as shown in Table 3.

TABLE 3

Effect of isobutyronitrile content of feed to product column on methacrolein content and hydrogen cyanide content of product.

| | Isobutyronitrile content | | Impurities content in product | | Amount of acetic acid added to top of product column, (ppm by wt.) | pH of condensate |
|---|---|---|---|---|---|---|
| | Feed to product column (ppm by wt.) | Bottom Stream of product column (ppm by wt.) | Methacrolein (ppm by wt.) | Hydrogen cyanide (ppm by wt.) | | |
| Example | | | | | | |
| 1 | 12 | 35 | 18 | 8 | 0 | 5.1 |
| 2 | 82 | 313 | 50 | 16 | 0 | 4.9 |
| 3 | 85 | 347 | 27 | 10 | 2,000 | 3.8 |
| Comparative Example | | | | | | |
| 1 | 888 | 3,217 | 249 | 56 | 0 | 5.2 |
| 2 | 9,155 | 27,225 | 701 | 154 | 0 | 5.8 |

EXAMPLE 3

A 100-g portion of a methacrylonitrile solution containing methacrolein cyanohydrin and acetic acid was placed in a 300-ml flask and kept at 85° C. Upon determination of the percentage decomposition of the cyanohydrin, it was found that the percentage decomposition of the cyanohydrin was markedly increased by the addition of isobutyronitrile, as shown in Table 4.

TABLE 4

Percentage decomposition of cyanohydrin in the presence of isobutyronitrile.

| | (A) Solution containing isobutyronitrile pH 3.7 | (B) Solution free from isobutyronitrile pH 1.1 |
|---|---|---|
| Percentage decomposition of cyanohydrin | 22% ($\theta$ = 25 hr.) 33% ($\theta$ = 50 hr.) | ≈0% ($\theta$ = 25 hr. and 50 hr.) |

| Composition of test solution: | | Wt. % |
|---|---|---|
| (A) | Methacrylonitrile | 84 |
| | Methacrolein cyanohydrin | 1 |
| | Acetic acid | 5 |
| | Isobutyronitrile | 10 |
| | Hydroquinone | 1,000 ppm (wt.) |
| (B) | Methacrylonitrile | 94 |
| | Methacrolein cyanohydrin | 1 |
| | Acetic acid | 5 |
| | Hydroquinone | 1,000 ppm (wt.) |

What is claimed is:

1. In a process for the recovery of purified methacrylonitrile from a mixture of methacrylonitrile with other olefinic nitriles, said mixture being produced by vapor phase ammoxidation of isobutylene or tert-butyl alcohol with ammonia and oxygen, and wherein said mixture has been absorbed by a water solvent in an absorption column, the process comprising:
   (a) feeding the resulting absorbed aqueous solution of said mixture to a recovery column, wherein said solution is extractively distilled with water;
   (b) removing as the overhead of said recovery column a vapor stream which is condensed to form a two-phase liquid distillate having an aqueous layer and an organic oil layer;
   (c) separating the recovery column overhead organic oil layer from the aqueous layer;
   (d) returning the separated aqueous layer to the recovery column;
   (e) feeding the separated organic oil layer to a de-hydrogen cyanide/dehydration column;
   (f) removing hydrogen cyanide from the overhead of the de-hydrogen cyanide/dehydration column;
   (g) removing from the de-hydrogen cyanide/dehydration column, a two-layer, aqueous and organic sidestream;
   (h) separating the de-hydrogen cyanide/dehydration column sidestream organic layer from the aqueous layer;
   (i) removing crude methacrylonitrile as the bottoms of the de-hydrogen cyanide/dehydration column;
   (j) feeding the crude methacrylonitrile to a high-boiling fraction separation column, the improvement comprising:
   (k) removing isobutyronitrile from the crude methacrylonitrile by withdrawing as the bottoms of the high-boiling fraction separation column an organic liquid stream of isobutyronitrile and other high-boiling impurities;
   (l) removing as the overhead of the high-boiling fraction separation column a vapor stream of methacrylonitrile and other low-boiling components, and condensing said vapor stream to a liquid distillate;
   (m) feeding the high-boiling fraction separation column liquid distillate to the lower half of a product column;
   (n) removing as the overhead of the product column a vapor stream of methacrolein and other low-boiling components, condensing said vapor to a liquid, and recyling said liquid to the top of the product column;
   (o) removing as the bottoms of the product column a liquid stream of residual high-boiling components and recycling said liquid stream to the recovery column, and;
   (p) removing purified methacrylonitrile from the lower half of the product column as a vapor sidestream.

2. In a process for the recovery of purified methacrylonitrile from a mixture of methacrylonitrile with other olefinic nitriles, said mixture being produced by vapor phase ammoxidation of isobutylene or tert-butyl alcohol with ammonia and oxygen, wherein said mixture has been absorbed by a water solvent in an absorption column, and wherein the resulting absorbed aqueous solution of said mixture is fed to a recovery column, where said solution is extractively distilled with water, the improvement comprising:

separating isobutyronitrile from the absorbed aqueous solution and removing isobutyronitrile from the process by:

(1) operating the recovery column such that isobutyronitrile is caused to accumulate in the bottom of said column;

(2) withdrawing the accumulated isobutyronitrile with the water from the bottom of said recovery column as a concentrated aqueous isobutyronitrile solution;

(3) conducting said concentrated aqueous isobutyronitrile solution to the absorption column; and (4) removing the isobutyronitrile from the absorption column overhead.

3. The process of claim 1, further comprising suppressing the undesirable formation of methacrolein cyanohydrin, which occurs in the product column condensed overhead as a result of the reaction of methacrolein with hydrogen cyanide, promoted by the presence of water, by reducing the water content of said condensed overhead to below the saturated level at which the condensate cannot separate into an aqueous layer and an oil layer, and by controlling the degree of dehydration performed in the dehydrogen cyanide/dehydration column so that the water content of the crude methacrylonitrile stream exiting the bottom of said column is kept at about 0.2 weight percent or less.

4. The process of claim 1 further comprising suppressing the undesirable formation of methacrolein cyanohydrin, which occurs in the product column condensed overhead as a result of the reaction of methacrolein with hydrogen cyanide, promoted by the presence of water, by adjustment of the pH of the product column condensate to within the range of from about 1.0 to 4.5.

5. The process of claim 4 wherein the pH is controlled by the addition of an organic acid to the product column condensed overhead.

6. The process of claim 5, wherein the organic acid is acetic acid or propionic acid.

7. A process according to claim 1, wherein the solution to be fed to the product column contains 200 ppm by weight or less of isobutyronitrile.

8. A process according to claim 1, wherein the solution to be fed to the product column contains 100 ppm by weight or less of isobutyronitrile.

9. A process according to claim 1, wherein the solution to be fed to the product column contains 50 ppm by weight or less of isobutyronitrile.

* * * * *